(12) United States Patent
Maris et al.

(10) Patent No.: US 10,743,497 B2
(45) Date of Patent: Aug. 18, 2020

(54) WHITE RUST RESISTANT CHRYSANTHEMUM PLANTS

(71) Applicant: Dümmen Group B.V., De Lier (NL)

(72) Inventors: Paulus Cornelis Maris, De Lier (NL); Peter Wain, Fareham (GB)

(73) Assignee: Dümmen Group B.V., De Lier (NL)

( * ) Notice: Subject to any disclaimer, the term of this patent is extended or adjusted under 35 U.S.C. 154(b) by 151 days.

(21) Appl. No.: 15/764,412

(22) PCT Filed: Oct. 4, 2016

(86) PCT No.: PCT/EP2016/073671
§ 371 (c)(1),
(2) Date: Mar. 29, 2018

(87) PCT Pub. No.: WO2017/060238
PCT Pub. Date: Apr. 13, 2017

(65) Prior Publication Data
US 2018/0352773 A1      Dec. 13, 2018

(30) Foreign Application Priority Data

Oct. 6, 2015   (NL) ..................................... 2015575
Apr. 4, 2016   (WO) ................. PCT/EP2016/057327

(51) Int. Cl.
*A01H 6/14*     (2018.01)
*A01H 5/02*     (2018.01)

(52) U.S. Cl.
CPC ............. *A01H 6/1424* (2018.05); *A01H 5/02* (2013.01)

(58) Field of Classification Search
CPC .................................................... A01H 6/1424
See application file for complete search history.

(56) References Cited

U.S. PATENT DOCUMENTS

PP6,737 P   *   4/1989   Van der Knapp ... A01H 6/1424

OTHER PUBLICATIONS

Martin et al Plant Pathology vol. 19 No. 4, pp. 180-184 (Year: 1970).*
De Jong et al Euphytica vol. 35, pp. 945-952 (Year: 1986).*
De Backer, "Characterization and detection of Puccinia horiana on chrysanthemum for resistance breeding and sustainable control", PhD thesis, Ghent University, 2012, 232 Pages, Belgium.
Martin et al., "Resistance of Chrysanthemum Cultivars to White Rust (*Puccinia horiana*)", Pl. Path., 1970, pp. 180-184, vol. 19.

* cited by examiner

*Primary Examiner* — David H Kruse
(74) *Attorney, Agent, or Firm* — The Webb Law Firm

(57) ABSTRACT

Provided herein are white rust resistant plants of the genus *Chrysanthemum* and seeds, plant parts, plant cells and progeny thereof. Also provided herein are markers for identifying white rust resistant plants of the genus *Chrysanthemum*. Specifically, the present invention relates to plant belonging to the genus *Chrysanthemum*, the plants are resistant to white rust and the plants comprise in their genome at least one genomic region, or gene or allele, providing white rust resistance, the white rust resistance providing genomic region, or gene or allele, is genetically linked to a nucleic acid sequence comprised in at least one copy in the genome of the resistant plants and is represented by SEQ ID No. 2.

10 Claims, No Drawings

Specification includes a Sequence Listing.

SEQUENCE LISTING

```
<160> NUMBER OF SEQ ID NOS: 2

<210> SEQ ID NO 1
<211> LENGTH: 192
<212> TYPE: DNA
<213> ORGANISM: Chrysanthemum <genus>

<400> SEQUENCE: 1
ttaactcaaa aatatgacta caaatcaatt ttcaggactt tttttcgata cttccctctt      60
tggtaccggt accgtattag tggtaccgat tttttttggg ctcaattcat ggtacaggca     120
ccgtaccgtg tattgggagt cggtaccgtt tcgatacggt accggtacgg ttccgattcg     180
ataccggaat tc                                                         192
```

-continued

```
<210> SEQ ID NO 2
<211> LENGTH: 180
<212> TYPE: DNA
<213> ORGANISM: Chrysanthemum <genus>

<400> SEQUENCE: 2
gaattcctat acgaaggttt tgtagatgtg tctccgagcg agtttgatcc taactcacga      60
ctagtaattt atgtccataa aaccgataac ttgaacattc cctcttgttc ttgtagatgg     120
ggatgacttc actgagtctc cattcttctg gcatcttatc actggaaaaa atcttgttaa     180
```

WHITE RUST RESISTANT CHRYSANTHEMUM PLANTS

CROSS-REFERENCE TO RELATED APPLICATIONS

This application is the United States national phase of International Application No. PCT/EP2016/073671 filed Oct. 4, 2016, and claims priority to Dutch Patent Application No. 2015575 and International Application No. PCT/EP2016/057327, filed Oct. 6, 2015, and Apr. 4, 2016, respectively, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1802675_ST25.txt. The size of the text file is 1,033 bytes, and the text file was created on Mar. 22, 2018.

The present invention relates to white rust resistant plants of the genus *Chrysanthemum* and to seeds, plant parts, plant cells and progeny thereof. The present invention further relates to means, and particularly molecular markers, for identifying white rust resistant plants of the genus *Chrysanthemum*.

Chrysanthemums, also designated as chrysant(h)s, are flowering plants of the genus *Chrysanthemum* in the family Asteraceae. The plants are native to Asia and north-eastern Europe and are comprised of a large number of horticultural varieties and cultivars.

Several genera of Chrysanthemums amongst which the economically important florist's Chrysanthemums were classified in the genus *Dendranthema* in the past. However, presently, the florist's Chrysanthemums are reclassified as *Chrysanthemum indicum*, restoring the position of these Chrysanthemums in the genus *Chrysanthemum*.

Naturally occurring *Chrysanthemum* species are herbaceous perennial plants. These *Chrysanthemum* species display alternately arranged leaves divided into leaflets with toothed or occasionally smooth edges. Chrysanthemums were first cultivated in China as a flowering herb as far back as the 15th century BC and over 500 cultivars had been recorded by the year 1630.

Presently cultivated Chrysanthemums display a more pronounced and aesthetic flowering as compared to their wild relatives. The flower heads occur in various forms, and can be daisy-like or decorative, like pompons or buttons. This genus contains many hybrids and thousands of cultivars developed for horticultural purposes. In addition to the traditional yellow, other colours are available, such as white, purple, and red. The most important hybrid is *Chrysanthemum* x *morifolium*, also designated as *Chrysanthemum* x *grandiflorum*, being primarily derived from *Chrysanthemum indicum*.

Chrysanthemums can be divided into two basic groups, garden hardy and exhibition. Garden Chrysanthemums are perennials capable of wintering in most northern latitudes. Exhibition varieties are generally not capable of surviving winter. Garden Chrysanthemums can be defined by their ability to produce an abundance of small blooms with little if any mechanical assistance, such as staking, and being able to withstand wind and rain. Exhibition varieties generally require staking, overwintering in a relatively dry, cool environment, and sometimes the addition of night lights.

White rust is a disease in plants caused by Basisiomycota. Basisiomycota form a distinct phylogenetic lineage of fungus-like eukaryotic microorganisms. They are filamentous, microscopic, absorptive organisms that reproduce both sexually and asexually. Basiodiomycetes occupy both saprophytic and pathogenic lifestyles, and include some of the most notorious pathogens of plants, causing devastating diseases such as southern blight of potato, tomato and a wide range of ornamentals and stem rust of wheat. The basidiomycetes are best known for the production of large fruit bodies such as mushrooms, puffballs and brackets and are important organisms in the decay of wood and leaf litter.

In *Chrysanthemum*, white rust is a disease generally caused by the pathogenic basidiomycete, or fungus, *Puccinia horiana*. *Chrysanthemum* specific symptoms include white rust spots on the upper surfaces of leaves. These spots are initially pale-green to yellow in colour and up to 5 mm in diameter, but may turn brown as the tissue becomes necrotic. On the underside of the leaf, the spots develop into pink or white pustules that become prominent as the teliospores develop. The disease is generally carried on infected cuttings and plants, including cut flowers, of glasshouse Chrysanthemums.

Until 1963, *Puccinia horiana* was confined to China and Japan. However, it has since spread rapidly on infected imported cuttings and is now a feared and serious disease in nurseries in Europe. A large number of pathotypes of *P. horiana* is known, and great differences of virulence of pathotypes of *P. horiana* after inoculation on various *Chrysanthemum* cultivars was demonstrated (De Backer, 2012). The *P. horiana* pathotype NL1, collected in 2006 in The Netherlands showed to be the most virulent one.

Preventive spraying with fungicides is effective but costly. When the climate is very suitable for white rust even preventive sprays are not effective enough and susceptible varieties are highly likely to be infected. Active ingredients found useful include oxycarboxin, triforine, benodanil, triadimefon, diclobutrazol, bitertanol and propiconazole. *Verticillium lecanii* has been suggested for biological control of on glasshouse Chrysanthemums.

Considering the considerable damage to *Chrysanthemum* cultivation by white rust, there is a need in the art to provide new genetic resistant sources, i.e. there is a need in the art for new resistance genes or alleles providing durable white rust resistance to plants of the genus *Chrysanthemum*.

It is an object of the present invention, amongst other objects, to meet the above need of the art.

According to the present invention, this object is met by the present invention by providing plants, plant parts, seeds and means as outlined in the appended claims.

Specifically, according to a first aspect, this object of the present invention, amongst other objects, is met by providing plants belonging to the genus *Chrysanthemum*, the plants are resistant to white rust and the plants comprise in their genome at least one genomic region, or gene or allele, providing white rust resistance, the white rust resistance providing genomic region, or gene or allele, is genetically linked to a nucleic acid sequence comprised in the genome of the resistant plants represented by SEQ ID No. 2. Considering the hexaploid nature of plants belonging to the genus *Chrysanthemum*, SEQ ID No. 2 is preferably present in the genome of the resistant plants in at least one copy, such as 2, 3, 4, 5 or 6 copies per resistant plant.

Preferably, the present plants further comprise in their genome a further genomic region, or gene or allele, providing white rust resistance, the further white rust resistance providing genomic region, or gene or allele, is genetically linked to a nucleic acid sequence comprised in at least one copy the genome of the resistant plants represented by SEQ ID No. 1. Considering the hexaploid nature of plants belonging to the genus *Chrysanthemum*, SEQ ID No. 1 is preferably present in the genome of the resistant plants in at least two copies, such as 3, 4, 5 or 6 copies.

The sequences of SEQ ID No. 1 and SEQ ID No. 2 are genetically linked to white rust resistances providing genomic regions, also designated herein as alleles or genes, or formulated differently, SEQ ID No 0.1 and SEQ ID No. 2 are molecular markers indicative for the presence of white rust resistance genomic regions, alleles or genes. SEQ ID No. 1 and SEQ ID No. 2 can, for example, be obtained by submitting a sample comprising genomic DNA of a white rust resistant plant of the genus *Chrysanthemum* to a restriction digestion with the restriction enzymes Mse1 and EcoR1 optionally in combination a nucleic acid amplification using primers pairs developed based on the sequences provided herein.

Although detecting the presence of SEQ ID No. 1 and/or SEQ ID No. 2 is sufficient to establish whether a plant of the genus *Chrysanthemum* is resistant to white rust, the resistance can additionally be confirmed by a disease assay such as the disease assay outlined below.

A disease assay can be conducted on cuttings or small plants inside closed plastic containers 125 cm length×80 cm width×35 cm height using a plastic cover. White rust infected inoculum plants are placed in the containers (36 inoculum plants per aquarium evenly distributed among 265 cuttings). An isolate derived from *P. horiana* pathotype NL1 was used; the original NL1 pathotype was obtained from the Plantenziektenkundige Dienst, Wageningen, NL. Because white rust requires a high relative humidity and a water film on the leaves, the small plants or cuttings, the inner sides of the plastic container and the cover are preferably fogged with demineralized water in combination with a wet cloth on the bottom of the plastic container. After preparing the experimental setup, the containers are placed in a growth chamber at 18° C. covered with white plastic to create a dark, humid environment for four days. Every day the containers are ventilated to ensure a good dispersal of the spores through the whole aquarium. After removing the white plastic the containers are illuminated with a combination of mercury and SON-T lights during 18 hours per day (6000 Lux). Generally, disease symptoms can be assessed 21 to 28 days post infection. Plants are scored according to a scale of 1 (infection) to 9 (not infected) wherein a scores of 1-3 indicate the plant as being susceptible, 4-6 indicates the plant as being intermediate resistant and 7-9 indicates the plant as being resistant.

The present plants are preferably a cut *Chrysanthemum* plant or a pot *Chrysanthemum* plant. Cut *Chrysanthemum* plants and pot *Chrysanthemum* plants are also designated in the art as cut flowers and potted plants, respectively. Sometimes, also reference is made to garden Chrysanthemums being a garden proof version of a pot *Chrysanthemum* plant.

According to a preferred embodiment of the invention, the present plants belonging to the genus *Chrysanthemum* are selected from the group consisting of *Chrysanthemum* x *morifolium; Chrysanthemum* x *grandiflorum; Chrysanthemum* x *rubellum; Chrysanthemum abolinii; Chrysanthemum achillaea* L.; *Chrysanthemum alabasicum; Chrysanthemum brachyanthum; Chrysanthemum carinatum; Chrysanthemum chalchingolicum; Chrysanthemum cinerariifolium; Chrysanthemum coccineum; Chrysanthemum coreanum; Chrysanthemum coronarium; Chrysanthemum decaisneanum; Chrysanthemum delavayanum; Chrysanthemum dichrum; Chrysanthemum fastigiatum; Chrysanthemum frutescens; Chrysanthemum gracile; Chrysanthemum grubovii; Chrysanthemum horaimontanum; Chrysanthemum hypoleucum; Chrysanthemum indicum* L.; *Chrysanthemum junnanicum; Chrysanthemum kinokuniense; Chrysanthemum kokanicum; Chrysanthemum konoanum; Crysanthemum majus; Chrysanthemum marginatum; Chrysanthemum mawei; Chrysanthemum maximum* L.; *Chrysanthemum miyatojimense; Chrysanthemum morifolium; Chrysanthemum multifidum; Chrysanthemum nitidum; Chrysanthemum parvifolium; Chrysanthemum przewalskii; Chrysanthemum purpureiflorum; Chrysanthemum ramosum; Chrysanthemum rhombifolium; Chrysanthemum roborowskii; Chrysanthemum segetum; Chrysanthemum shihchuanum; Chrysanthemum shimotomaii; Chrysanthemum trilobatum; Chrysanthemum tripinnatisectum; Chrysanthemum vestitum; Chrysanthemum vulgare* (L.); *Chrysanthemum yoshinyanthemum*; and *Chrysanthemum zawadskii*.

According to another preferred embodiment of the present invention, the causative pathogen causing the present white rust disease is *Puccinia* horiana. *Puccinia* horiana is an autoecious rust. The bicellular teliospores germinate in situ to produce unicellular basidiospores which are dispersed in air currents. No other spores are known. High humidity, and a film of moisture, appear to be necessary for the germination of both teliospores and basidiospores. Teliospores are capable of germination as soon as they are mature; germination and discharge of basidiospores occur between 4° C. and 23° C. and, at an optimum temperature of 17° C., discharge of basidiospores is observed within 3 hours. Basidiospores can germinate over a wide temperature range and, at 17-24° C., either surface of the leaf may be penetrated within 2 hours. Thus, only 5 hours of wetness is sufficient for a new infection to become established. Within the leaf, abundant, hyaline, intercellular hyphae are produced with intracellular haustoria. The incubation period is normally 7-10 days, but short periods of high temperatures (over 30° C.) can prolong the period to 8 weeks.

Following infection, pale-green to yellow spots, up to 5 mm in diameter, develop on the upper surface of leaves. The centres of these spots become brown and necrotic with aging. On the corresponding lower surface, raised, buff or pinkish, waxy pustules (telia) are found. As the spots on the upper surface become sunken, these pustules become quite prominent and turn whitish when basidiospores are produced. Telia are occasionally found on the upper leaf surface. Severely attacked leaves wilt, hang down the stem and gradually dry up completely.

According to yet another preferred embodiment, the present invention relates to plants having a resistance to white rust substantially similar to, or equivalent with, the resistance to white rust of a *Chrysanthemum* plant deposited under number NCIMB 42455 on Mar. 14, 2016. These plants can be readily identified by comparing white rust disease resistance, for example using a disease assay as described herein although other know white rust disease assays can be used. A *Chrysanthemum* plant deposited under number NCIMB 42455 can be obtained through the National Collection of Industrial, Food and Marine Bacteria (NCIMB), Ferguson Building, Craibstone Estate, Bucksburn, Aberdeen AB21 9YA, United Kingdom.

According to a particularly preferred embodiment, the present plants have a resistance to white rust identical to the white rust resistance found in a *Chrysanthemum* plant deposited under number NCIMB 42455. Especially preferred are plants comprising at least one white rust resistance providing genomic region or gene, preferably at least two white rust resistance providing genomic regions or genes, derived from a *Chrysanthemum* plant deposited under number NCIMB 42455 wherein the presence of said white rust resistance providing genomic regions or genes is indicated by the presence of SEQ ID No. 1 or SEQ ID No. 2 in the genome of said plant. Formulated differently, SEQ ID No. 1 or SEQ ID No. 2 are molecular, or genomic, markers indicative for, thus genetically linked with, the present resistance providing genomic regions or genes which can, for example, be found in NCIMB 42455.

According to a yet another particularly preferred embodiment, the present plants comprise in their genome at least two white rust resistance providing genomic regions or genes, the first white rust resistance providing genomic region or gene is genetically linked to a genomic nucleic acid sequence comprised in said plant genome represented by SEQ ID No. 1 and the second white rust resistance providing genomic region or gene is genetically linked to a genomic nucleic acid sequence comprised in said plant genome represented by SEQ ID No. 2.

According to a most preferred embodiment, the present invention relates to a *Chrysanthemum* x *morifolium* plant, wherein the plant is resistant to the white rust pathogen *Puccinia horiana* and the white rust resistance is encoded by a first resistance providing genomic region or gene genetically linked to SEQ ID No. 1 and/or a second resistance providing genomic region or gene genetically linked to SEQ ID No. 2.

Considering the importance of white rust resistant genetic sources in the art, such as the present plants, the present invention, according to a second aspect, relates to seeds, plant parts or plant cells of the present plants. The present seeds, plant parts or plant cells comprise in their genome SEQ ID No. 2 or SEQ ID No. 2 and SEQ ID No. 1, preferably SEQ ID No. 1 and SEQ ID No. 2 and are, accordingly, capable of providing, or cultivated into, plants being resistant to white rust and especially white rust caused by an infection with *Puccinia* horiana.

According to a third aspect, the present invention also relates to progeny of the present *Chrysanthemum* plants. Progeny of the present plants can be readily identified by establishing the presence of SEQ ID No. 2, preferably SEQ ID No. 1 and SEQ ID No. 2, in their genome.

According to a fourth aspect, the present invention relates to the use of SEQ ID No. 1 or SEQ ID No. 2 for identifying a white rust resistant *Chrysanthemum* plant. Suitable methods, based on SEQ ID No. 1 or SEQ ID No. 2, for identifying such plant are generally known in the art such as methods based on nucleic acid amplification of genomic DNA and subsequent visualisation of amplification fragments although other techniques can be envisaged such as techniques based on hybridisation.

The present invention will be further detailed in the example presented below.

EXAMPLE

Introduction

Martin, P., & Firman, I. (1970). Resistance of *Chrysanthemum* Cultivars to White Rust (*Puccinia horiana*). Plant Pathology, 180-184 discloses several varieties of *Chrysantemum* white rust resistant plants. In order to asses whether the present genomic sequences linked white rust, i.e. SEQ ID Nos 1 and 2, are found in the disclosed *chrysanthemum* cultivars, these cultivars were subjected to marker analyses and the results are presented in Table 1 below:

TABLE 1

Phenotype after inoculation with NL1 isolate of *P. horiana* of *Chrysanthemum* varieties previously reported by Martin (1970) to be resistant or immune to *P. horiana*.

| Variety | Phenotype according to Martin (1970) | Phenotype | SEQ ID No. 1[2] | SEQ ID No. 2 |
|---|---|---|---|---|
| Alec Bedser | Immune | N.t.[1] | — | — |
| Fred Shoesmith | Immune | Susceptible | — | — |
| Marlene | Immune | Susceptible | — | — |
| Polaris | Immune | Susceptible | — | — |
| Regalia | Immune | N.t. | + | — |
| Streamer | Immune | Susceptible | N.t. | N.t. |
| Sweetheart | Immune | Susceptible | — | — |
| Target | Immune | N.t. | — | — |
| Vibrant[4] | Immune | N.t. | N.t. | N.t. |
| Bravo | Moderate resistant | Susceptible | N.t. | N.t. |
| Corsair | Practically immune | Susceptible | — | — |
| Discovery | Practically immune | Susceptible | — | — |
| Glamour | Practically immune | Resistant | + | — |
| Rivalry | Practically immune | Susceptible | — | — |

[1] N.t. = not tested
[2] —: SEQ ID is not present,
+: gene is present

As can be clearly seen, none of the above plants disclosed in Martin et al., comprise a genomic sequence represented by SEQ ID No. 2.

The invention claimed is:

1. A *Chrysanthemum* plant having resistance to white rust and comprising in its genome SEQ ID NO: 2, seed of said plant having been deposited under NCIMB Accession No. 42455.

2. The *Chrysanthemum* plant of claim 1, wherein the *Chrysanthemum* plant comprises in its genome SEQ ID NO: 1.

3. The *Chrysanthemum* plant of claim 1, wherein a causative pathogen of said white rust is *Puccinia horiana*.

4. Progeny of the *Chrysanthemum* plant of claim 1, wherein the progeny is resistant to white rust and comprises in its genome SEQ ID NO: 2.

5. The *Chrysanthemum* plant of claim 4, wherein said plant is a cut *Chrysanthemum* or said plant is a pot *Chrysanthemum*.

6. The *Chrysanthemum* plant of claim 4, wherein said plant is a *Chrysanthemum* x *morifolium* plant, said plant is resistant to the white rust pathogen *Puccinia horiana*, and said resistance is encoded by a first resistance providing genomic region, gene, or allele genetically linked to SEQ ID NO: 2 and a second resistance providing genomic region, gene, or allele, genetically linked to SEQ ID NO: 1.

7. A seed, plant part, or plant cell of the *Chrysanthemum* plant of claim 1, wherein the seed, plant part, or plant cell is resistant to white rust and comprises in its genome SEQ ID NO: 2.

8. A seed, plant part, or plant cell of the *Chrysanthemum* plant of claim 4, wherein the seed, plant part, or plant cell is resistant to white rust and comprises in its genome SEQ ID NO: 2.

9. A *Chrysanthemum* plant grown from seed deposited under NCIMB Accession No. 42455, wherein the *Chrysanthemum* plant is resistant to white rust and comprises in its genome SEQ ID NO: 2.

10. A seed, plant part, or plant cell of the *Chrysanthemum* plant of claim 9, wherein the seed, plant part, or plant cell is resistant to white rust and comprises in its genome SEQ ID NO: 2.

* * * * *